United States Patent
Murphy et al.

(10) Patent No.: US 11,543,481 B2
(45) Date of Patent: Jan. 3, 2023

(54) METHODS FOR ESTIMATING MECHANICAL PROPERTIES FROM MAGNETIC RESONANCE ELASTOGRAPHY DATA USING ARTIFICIAL NEURAL NETWORKS

(71) Applicant: Mayo Foundation for Medical Education and Research, Rochester, MN (US)

(72) Inventors: Matthew C. Murphy, Rochester, MN (US); Richard L. Ehman, Rochester, MN (US); Kevin J. Glaser, Rochester, MN (US); Joshua D. Trzasko, Rochester, MN (US); Armando Manduca, Rochester, MN (US); John Huston, III, Rochester, MN (US); Jonathan M. Scott, Rochester, MN (US); Arvin Forghanian-Arani, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 299 days.

(21) Appl. No.: 16/764,838

(22) PCT Filed: Nov. 19, 2018

(86) PCT No.: PCT/US2018/061779
§ 371 (c)(1),
(2) Date: May 15, 2020

(87) PCT Pub. No.: WO2019/099986
PCT Pub. Date: May 23, 2019

(65) Prior Publication Data
US 2020/0341098 A1    Oct. 29, 2020

Related U.S. Application Data

(60) Provisional application No. 62/588,115, filed on Nov. 17, 2017.

(51) Int. Cl.
*G01R 33/563* (2006.01)
*A61B 5/055* (2006.01)
(Continued)

(52) U.S. Cl.
CPC ........ *G01R 33/56358* (2013.01); *A61B 5/055* (2013.01); *A61B 5/7267* (2013.01);
(Continued)

(58) Field of Classification Search
None
See application file for complete search history.

(56) References Cited

U.S. PATENT DOCUMENTS

| 11,284,827 | B2 * | 3/2022 | Telenkov | ............... A61B 5/316 |
| 2006/0012367 | A1 * | 1/2006 | Meaney | ............... A61B 5/0507 |
| | | | | 324/315 |

(Continued)

OTHER PUBLICATIONS

Chen, Y., et al. "Trainable nonlinear reaction diffusion: A flexible framework for fast and effective image restoration." IEEE transactions on pattern analysis and machine intelligence 39.6 (2016): 1256-1272.
(Continued)

*Primary Examiner* — Rodney E Fuller
(74) *Attorney, Agent, or Firm* — Quarles & Brady LLP (57) ABSTRACT

Magnetic resonance elastography ("MRE"), or other imaging-based elastography techniques, generate estimates of the mechanical properties, such as stiffness and damping ratio, of tissues in a subject. A machine learning approach, such as an artificial neural network, is implemented to perform an
(Continued)

inversion of displacement data in order to generate the estimates of the mechanical properties.

24 Claims, 5 Drawing Sheets

(51) Int. Cl.
    *A61B 5/00*     (2006.01)
    *G01R 33/30*     (2006.01)
    *G01R 33/56*     (2006.01)
    *G06N 3/04*     (2006.01)
    *G06N 3/08*     (2006.01)

(52) U.S. Cl.
    CPC ....... *G01R 33/307* (2013.01); *G01R 33/5608* (2013.01); *G06N 3/04* (2013.01); *G06N 3/08* (2013.01)

(56) References Cited

U.S. PATENT DOCUMENTS

| 2017/0281094 | A1 | 10/2017 | Ghaboussi | |
| 2020/0205739 | A1* | 7/2020 | Garrett | G16H 50/30 |
| 2020/0205745 | A1* | 7/2020 | Khosousi | A61B 5/7275 |
| 2020/0211713 | A1* | 7/2020 | Shadforth | G06T 7/13 |
| 2020/0401938 | A1* | 12/2020 | Etkin | G06V 10/768 |
| 2021/0049757 | A1* | 2/2021 | Zhu | G06T 7/0012 |

OTHER PUBLICATIONS

Glaser, K. J., et al. "Review of MR elastography applications and recent developments." Journal of Magnetic Resonance Imaging 36.4 (2012): 757-774.

Hoerig, C., et al. "Data-driven elasticity imaging using cartesian neural network constitutive models and the autoprogressive method." IEEE transactions on medical imaging 38.5 (2018): 1150-1160.

International Searching Authority, International Search Report and Written Opinion for application PCT/US2018/061779, dated Feb. 28, 2019.

Lecun Y, et al. Deep learning. Nature 2015;521(7553):436-444.

Moller MF. A Scaled Conjugate-Gradient Algorithm for Fast Supervised Learning. Neural Networks 1993;6(4):525-533.

Murphy MC, et al. Artificial neural networks for slifiless estimation in magnetic resonance elastography. Magnetic Resonance in Medicine 80:351-360. 2018.

\* cited by examiner

METHODS FOR ESTIMATING MECHANICAL PROPERTIES FROM MAGNETIC RESONANCE ELASTOGRAPHY DATA USING ARTIFICIAL NEURAL NETWORKS

CROSS-REFERENCE TO RELATED APPLICATIONS

This application is a 371 U.S. National Phase application of PCT/US2018/061779, filed Nov. 19, 2018, which claims the benefit of U.S. Provisional Patent Application Ser. No. 62/588,115, filed on Nov. 17, 2017, and entitled "METHODS FOR ESTIMATING TISSUE STIFFNESS FROM MAGNETIC RESONANCE ELASTOGRAPHY DATA USING ARTIFICIAL NEURAL NETWORKS," which is herein incorporated by reference in its entirety.

STATEMENT REGARDING FEDERALLY SPONSORED RESEARCH

This invention was made with government support under EB001981 awarded by the National Institutes of Health. The government has certain rights in the invention.

BACKGROUND

Magnetic resonance elastography ("MRE") is a magnetic resonance imaging ("MRI")-based technique for measuring tissue stiffness, akin to manual palpation, which has a long history in the practice of medicine. MRE includes introducing shear waves into a tissue-of-interest by mechanical vibration. Next, the resulting tissue displacement is imaged by a phase-contrast MRI pulse sequence with motion encoding gradients that are synchronized to the motion. Finally, these displacement images are mathematically inverted to calculate tissue stiffness.

MRE is growing in clinical impact, particularly for applications in the liver, where it is used to noninvasively assess fibrosis with high accuracy. Furthermore, brain stiffness has shown sensitivity to a number of physiological processes including neurodegenerative disease, normal aging, and even behavioral performance. Still, there remains a motivation to improve the effective resolution and robustness of MRE to enable further investigation into the spatial relationship between tissue mechanical properties and pathophysiology, and to open up new applications in focal diseases.

Elastography can also be performed with other imaging modalities, such as ultrasound and some optical techniques. Many of these elastography techniques are similar to MRE in the sense that shear waves are introduced into the tissue, or material, and the resulting displacements are measured by the imaging modality. To this end, the inversion algorithms used to compute stiffness and other mechanical properties from these displacement data, and the issues facing such algorithms, are similar to those faced in MRE.

Currently, the inversion algorithms used to compute stiffness from the displacement data represent one of the greatest limitations on the resolution of MRE and other elastography techniques. A number of methods exist for performing the inversion calculation, each with its unique set of advantages and disadvantages. Popular algorithms in the field include, but are not limited to, variations of direct inversion ("DI"), local frequency estimation, and non-linear inversion. Each model relies on underlying assumptions that will impact its performance in in vivo data, as well as a number of implementation choices (e.g., tuning parameters and filter settings) that affect the tradeoff between resolution and numerical stability. An algorithm that can provide stable estimates in the presence of noise while maintaining a small spatial filtering footprint could substantially improve the effective resolution of MRE and other elastography techniques, either by mitigating the need for smoothing or by allowing reliable estimation in smaller regions.

SUMMARY OF THE DISCLOSURE

The present disclosure addresses the aforementioned drawbacks by providing a method for generating an image that depicts a mechanical property in a tissue of a subject. Displacement data are provided to a computer system, the displacement data having been acquired with a magnetic resonance imaging ("MRI") system and depicting displacements caused in a subject by vibratory motion applied to the subject while the subject was imaged with the MRI system. Training data representative of the displacement data are also provided to the computer system. A neural network is constructed and trained on the training data using the computer system. An image that depicts a mechanical property in a tissue of the subject is generated by inputting the displacement data to the trained neural network.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for magnetic resonance elastography ("MRE"), and other elastography techniques, in which a machine learning approach, such as an artificial neural network, is implemented to perform an inversion of displacement data in order to generate estimates of the mechanical properties of a subject. Using machine learning to implement inversion (e.g., MRE inversion) is advantageous because it is data-driven, and thus provides a framework for dealing with practical issues such as tissue inhomogeneity, partial volume effects, and noise. Moreover, predictions made from these models are effectively bounded by the training data, and thus provide stability when measuring stiffness in smaller regions.

As will be described, the systems and methods described in the present disclosure provide for the inversion of displacement data in a manner that provides stable mechanical property (e.g., stiffness, damping ratio) estimates in the presence of noise, does not require assumptions on local homogeneity, is computationally efficient when compared with previous inversion techniques, and is capable of inverting displacement data acquired at a single frequency, or at multiple frequencies.

Although other machine learning approaches can be implemented, artificial neural networks ("ANNs") have an advantage where the optimal preprocessing of the displacement data in order to estimate stiffness is not necessarily known ahead of time. ANNs with multiple hidden layers are capable of learning abstract representations of the inputs, which can then be utilized by deeper layers to estimate the quantity of interest. One non-limiting example of machine learning algorithms other than ANNs that can implement the methods described in the present disclosure include trained reaction diffusion networks.

Figure 1:
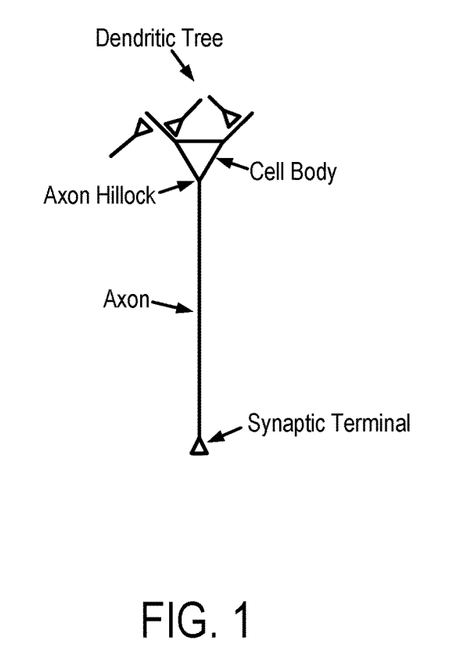
FIG. 1 is a schematic of an example neuron.

ANNs represent a class of function approximators inspired by neural networks found in the brain. A simple model of a neuron is shown in FIG. 1. Upstream neurons form synapses with this cell in the dendritic tree, where the release of neurotransmitters will open ion channels and alter the membrane potential at the synaptic site. These electrical signals then passively propagate through the cell body to the axon hillock, where a decision is made about whether to generate an output signal (i.e., an action potential). Notably, upstream neurons have varying degrees of influence on this decision at the hillock depending on the distance to that particular synapse and the conduction properties of the dendritic tree along that path. If these postsynaptic potentials sum to a certain threshold potential, then voltage-gated ion channels will be opened at the hillock initiating the formation of an action potential. An action potential is a large spike in the membrane potential of the cell, which is propagated down the axon to initiate neurotransmitter release at the synaptic terminal, and thus influence the membrane potential of the downstream neuron.

Figure 2:
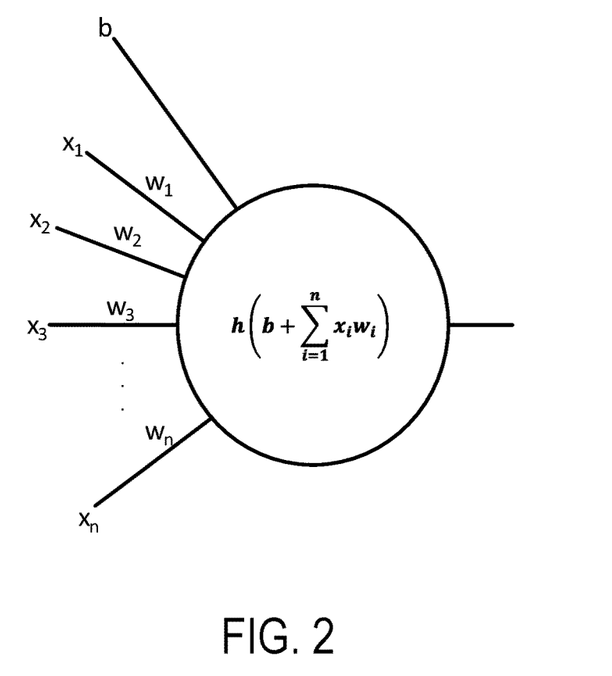
FIG. 2 is an example of a model neuron used in an artificial neural network, which computes the sum of the product of weights, w, and inputs, x, as well as a bias term, and then applies a nonlinear transfer function, h.

A schematic representation of a neuron is shown in FIG. 2 for the purpose of understanding the ANNs described in the present disclosure. The properties of this model neuron are that it first computes the weighted sum of input from upstream neurons (x) as well as a bias term (b), and then applies a nonlinear transfer function, h(x), to this value, and then sends this output to downstream neurons. As one non-limiting example, the transfer function, h(x), can be a hyperbolic tangent transfer function (also called an activation function), though several other candidate functions can also be readily implemented. For example, a rectified linear unit ("RELU") action function could also be used.

Figure 3:
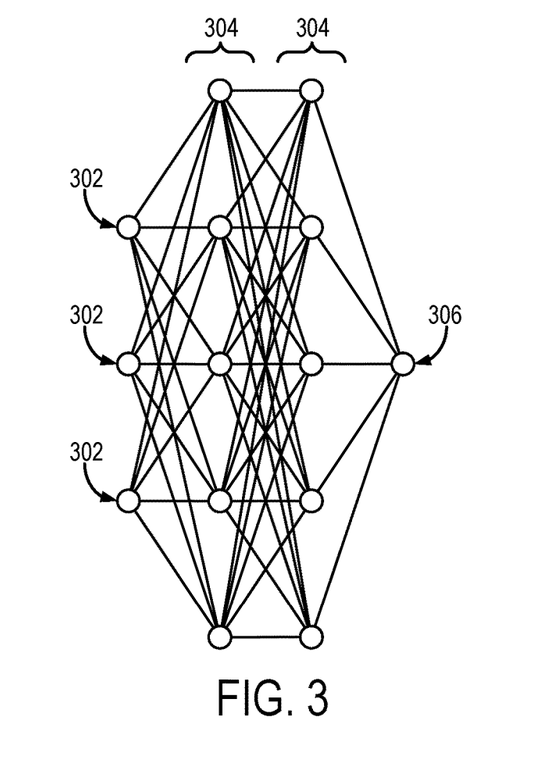
FIG. 3 is a diagram of an example feedforward neural network with three inputs, two hidden layers with five units in each, and a single output.

One example of an ANN architecture that can be implemented by the methods described in the present disclosure is a feedforward neural network with fully-connected layers. An example feedforward ANN is shown in FIG. 3. This example feedforward ANN has three inputs 302 (or features), two hidden layers 304 with five neurons in each hidden layer 304, and a single neuron in the output layer 306. In this type of ANN, each neuron receives input from every neuron in the previous layer, and sends its output to every neuron in the following layer. Each of these neurons can operate as the model shown in FIG. 2. In another example, the ANN can include more than two hidden layers (e.g., three or more hidden layers) and each hidden layer can contain fewer than, or more than, five neurons. The ANN can also include other layers in addition to the two or more hidden layers. For instance, the ANN could include convolutional layers, activation or nonlinear layers, dropout layers, pooling layers (e.g., max pooling layers), and so on. One or more of the layers in the ANN may be fully connected layers.

The weights of the ANN are learned through a training process. As one non-limiting example of a training process, in the case of supervised training, the weights are adjusted iteratively by a backpropagation method (e.g., a scaled gradient backpropagation or other backpropagation technique) using a training set that contains features and known desired outputs. In this example, the weights are initialized with small, random values. Then, the ANN is evaluated in the forward direction and the error is calculated between the ANN prediction and the known target values provided by the training set. Next, the gradient of the error with respect to each weight is computed in the backward direction, beginning with the output layer and working progressively upstream, each time using the previously computed gradients to calculate errors in the immediately upstream-layer according to the chain rule. With the error and gradients computed, any one of a number of nonlinear optimization algorithms can be used to update the weights for the next iteration. This process is repeated until a stopping criterion is reached. As one example, training can be stopped when the error is no longer reduced in a separate cross-validation set, such as when mean squared error is not improved in the validation set for a number of consecutive iterations.

Figure 4:
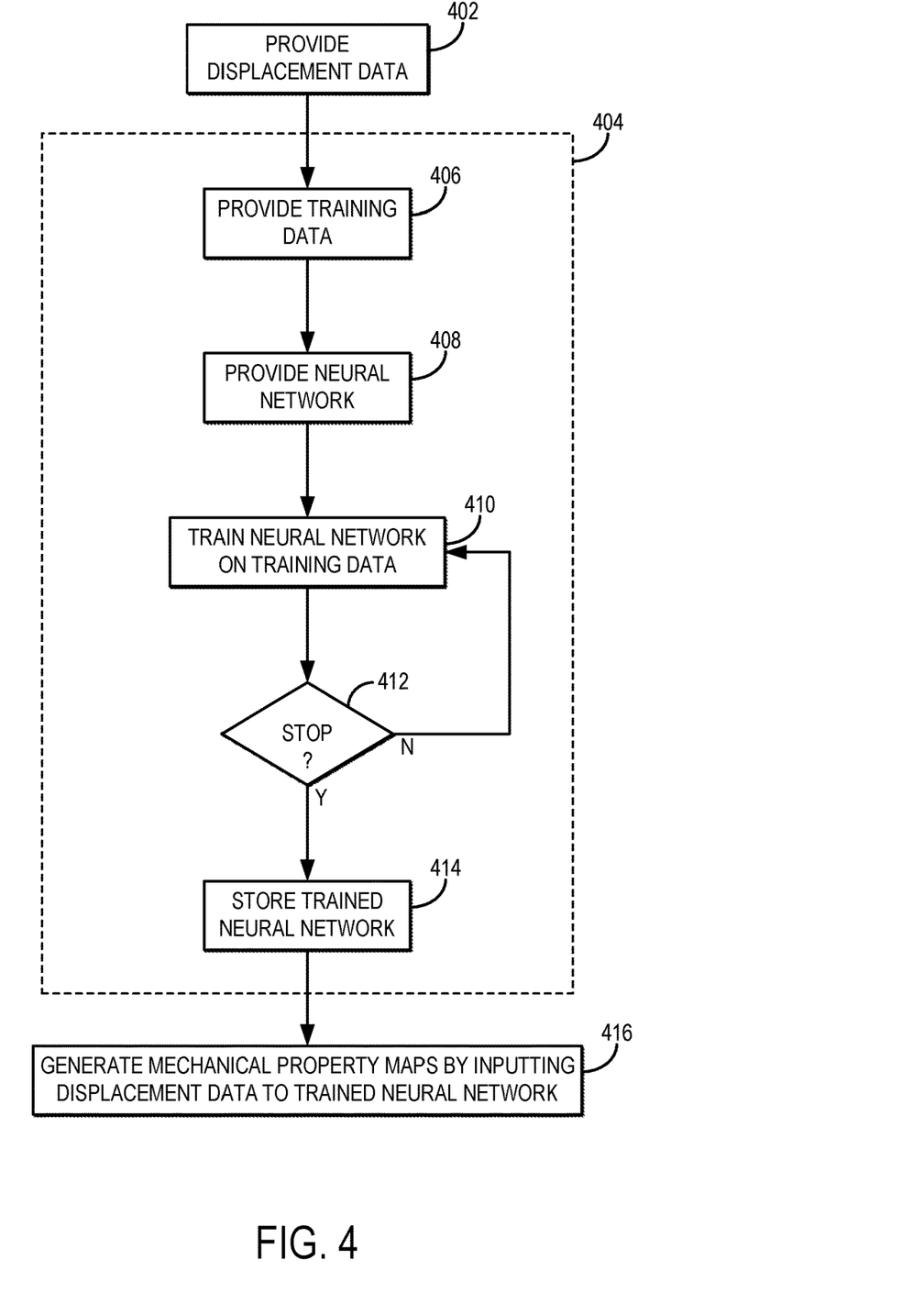
FIG. 4 is a flowchart setting forth the steps of an example method for generating a mechanical property map using magnetic resonance elastography ("MRE"), or another suitable elastography technique, to provide displacement data that are input to an artificial neural network trained to implement elastography inversion.

Referring now to FIG. 4, a flowchart is illustrated as setting forth the steps of an example method for generating images that depict mechanical properties in a subject by performing inversion (e.g., MRE inversion) on displacement data using an artificial neural network. Examples of mechanical properties that can be estimated using the methods described in the present disclosure include, but are not limited to, stiffness, storage modulus, loss modulus, damping ratio, poroelastic parameters, and so on. In some instances, the systems and methods described in the present disclosure can implement neural networks that are trained to estimate mechanical properties from more complicated rheological models (e.g., a Voigt model, poroelastic models, anisotropic models).

The method includes providing displacement data to a computer system, as indicated at step 402. The displacement data can include, for instance, wave images obtained using an MRE scan. The displacement data may be provided to the computer system by retrieving previously acquired displacement data from a memory or other suitable data storage. As another example, the displacement data may be provided to the computer system by acquiring displacement data using an MRI system that is in communication with the computer system. In some instances, the computer system may form a part of the MRI system. Such displacement data can be acquired by operating the MRI system to perform an MRE scan, such as those described in U.S. Pat. No. 5,592,085, which is herein incorporated by reference in its entirety. In still other embodiments, the displacement data can be obtained with other imaging modalities and techniques. For instance, the elastography data could be obtained using ultrasound elastography techniques or optical elastography techniques.

In general, the displacement data are representative of displacements occurring in the subject while the displacement data are acquired. In some instances, the displacement data may be representative of time-harmonic displacement fields. In some other instances, the displacement data may be representative of transient displacement fields.

The displacement data may represent displacements caused by a single wave source, or by multiple wave sources. More generally, the displacement data may represent displacements associated with a single wave field or with multiple wave fields. In some instances, the displacement data can represent simultaneous, multifrequency displacement.

A neural network is trained, as generally indicated at process block 404. In general, the neural network is trained on training data, which may be simulated data, displacement data acquired from a previous imaging session (e.g., a previous MRE scan), or some or all of the displacement data provided in step 402.

Thus, the training process can include providing suitable training data, as indicated at step 406. As mentioned, in some embodiments, the neural network can be trained on simulated data. For instance, simulated data can include patches of voxels containing simulated displacement data having a number of different phase offsets over one or more periods of motion. The patches may be one-dimensional, two-dimensional, or three-dimensional. As one non-limiting example, the simulated data can include 5×5 patches with 2-mm isotropic voxels and 4 phase offsets spaced evenly over one period of 60-Hz motion. Other patch sizes can also be implemented, such as 3×3, 7×7, 11×11, and soon. Three-dimensional patches can also be used, such as 5×5×5 sized patches. In some instances, the patch sizes are not symmetrical, such as patches with sizes m×n, m×m×n, m×n×p, or otherwise, where m≠n≠p. Voxel sizes other than 2-mm, whether isotropic or otherwise, can also be used. The stiffness values used for the simulated data can be chosen randomly. As an example, the stiffness values can be chosen randomly from a uniform distribution with a range of values, such as 0.1 to 10 kPa.

The simulated data can be generated using a simulation in which a single point-source is placed in a random location at a randomly assigned distance from the center of the patch. In some other instances, the simulated data can be generated using a simulation in which one or more point-sources are placed in random locations within a patch. Previous inversion techniques have difficulty estimating mechanical properties near wave sources; however, it is contemplated that the systems and methods described in the present disclosure can overcome these challenges and provide estimation of mechanical properties even near wave sources. A sinusoidal wave can be computed as a function of distance from that source to produce radially propagating waves with the appropriate wavelength attenuation. In other examples, multiple wave sources can be used. For instance, a random number of sources can each be placed at a random location within a simulation region. In these examples, the simulated displacements can be computed as the superposition of the multiple sources divided by the number of sources.

As one non-limiting example, the training data may include simulation data generated using a coupled harmonic oscillators ("CHO") simulation; however, other simulation techniques may also be used, including finite element models, finite difference models, and so on. Such simulation data may include a number of 2D data sets, 3D data sets, or combinations thereof. For instance, the simulation data may include 2D data sets that each include a patch of isotropic pixels or non-isotropic pixels. Advantageously, CHO simulations can be used to generate simulation data for displacement in an inhomogeneous medium.

In one example implementation, 70×70 patches with 2-mm isotropic pixels with a homogeneous background and an inclusion ranging in diameter from 1-10 cm placed in the center of the patch were used. In such examples, the stiffness of the background and the inclusion in each patch can be chosen randomly from a distribution, such as a uniform distribution from 1-10 kPa. In the example of using a CHO simulation to generate simulation data, a randomly selected number of harmonic force generators (e.g., 1-10) with an oscillation frequency (e.g., 100 Hz) can be placed at the boundary of the simulation. For instance, in some implementations, the simulation data can be generated to represent motion-type information around the boundaries of a region in order to estimate the properties of what is inside the region.

Damping can be assumed constant across all simulation, and can be assumed to be homogeneous within each simulation. In other implementations, however, the damping can be variable, inhomogeneous across each simulation, or both. The level of damping can be selected such that the wave from a single point source would travel across the entire simulation footprint before complete attenuation. Other levels of damping can also be selected as desired. As one example, a steady-state solution at four phase offsets equally distributed across one period of motion can be used to generate four displacement images for each data set.

In some embodiments, the training data can be augmented. For instance, some or all of the patches in the training data can be adjusted, manipulated, or otherwise processed. For example, patches from randomly selected locations can be further adjusted, manipulated, or processed. As one example, patches from randomly selected locations centered a number of pixels (e.g., one pixel) adjacent to the boundary of the inclusion, or on the boundary itself, can be selected. The selected patches can be rotated. For instance, the selected patches can each be rotated by a random number of degrees. As one example, the selected patches can each be rotated by a random multiple of 90 degrees. Other data augmentations, such as horizontal flips, vertical flips, random crops, translations, and so on, can also be implemented.

In some instances, noise can be added to the simulated data. For example, randomly chosen signal-to-noise ratio ("SNR") values can be selected from a distribution of such values, such as a uniform distribution in a range of 1 to 20. The noise may be pseudorandom noise with a Gaussian distribution, or other suitable forms of noise. The noise may have a zero mean, and may have a standard deviation that is scaled to provide the prescribed SNR values. The noise can be added to the simulated data.

As another example, the noise added to the simulated data may be structured to be more representative of noise commonly encountered in MRI. In these examples, the simulated displacements can be converted into system-specific and MRE sequence-specific phase values using MRE signal encoding models. This phase signal can then be additively combined with a synthetic low-order phase field that simulates susceptibility effects. A complex image can be generated using this simulated phase and a magnitude signal, which may be either an anatomical image or anatomically realistic binary mask. Finally, zero mean proper complex Gaussian noise can be added to this image. The MR-realistic MRE displacement image can be obtained using standard processing tools, such as phase differencing of images simulated with positive/negative motion encoding gradient pairs. The fundamental noise level (e.g., variance of complex Gaussian noise) for each training example can be assigned randomly from a uniform distribution with a range chosen to sufficiently stratify an expected range of magnitude SNRs, which may be measured from previous studies. Adding noise in this manner ensures that the simulated training data are statistically consistent with the MRI-based data which are later inputted to the neural network.

In some instances, the training data may include missing data. As an example, the training data may include patches of displacement data which are masked to remove some of the displacement data. For instance, randomly selected mask patches can be applied to patches of displacement data in order to generate masked displacement data patches. The mask patches can be selected from the acquired data, as an example. In such instances, the mask patches are preferably selected so as not to cross major anatomical boundaries. In the case of brain imaging, the mask patches can be selected so as not to cross boundaries such as the falx cerebri, the tentorium cerebelli, the Sylvian fissure, and the like.

The training process also includes providing the neural network to be trained, as indicated at step 408. Providing the neural network can include selecting the type of neural network and the corresponding parameters of that neural network. For instance, the neural network may be a feedforward neural network, a convolutional neural network, or other type of neural network. For instance, in some implementations the neural network may implement a variational sparse coding network or a convolutional sparse coding network. Parameters that can be selected include the types and numbers of layers, as well as the number of neurons in each layer, and so on.

The neural network is then trained on the provided training data, as indicated at step 410. Training can be performed on features extracted from the training data. For instance, the features given to the model for each observation, $x_i$, can include the real and imaginary parts of a temporal harmonic, such as the first temporal harmonic, of the displacement data in each patch of simulated data. In other implementations, the neural network can be trained directly on complex-valued data, rather than data with real and imaginary parts decoupled. In such instances, a phase-preserving complex transfer function can be used. The features can also be linearly scaled such that the range of $\pm|x_i|$ is mapped to the range $-1$ to $+1$. In still other implementations, the neural network can be trained directly on time offsets without computing the first temporal harmonic. As one example, the neural network model can be trained by fitting the training data to the neural network model a backpropagation technique, such as a scaled conjugate gradient backpropagation. As another example, the neural network can be trained using a stochastic optimization (e.g., a stochastic gradient descent). In some implementations, variance reduction setups, such as stochastic average gradient, can also be used. In some implementations, the training data are processed and the neural network is trained on the processed training data. As one example, the training data can be projected onto a basis before training.

A determination is made at decision block 412 whether a stopping criterion has been satisfied. If not, then another iteration of training the neural network occurs; otherwise, the trained neural network is stored, as indicated at step 414, for later use.

After the neural network is trained, the provided displacement data are input to the trained neural network to generate one or more mechanical property maps, as indicated at step 416. The mechanical property maps can include, for example, stiffness maps that provide quantitative information about the stiffness of tissues in the subject from which the displacement data were acquired. The mechanical property maps can also include, for example, damping ratio maps that provide quantitative information about the damping ratio of tissues in the subject from which the displacement data were acquired. Mechanical property maps are generated, for instance, by evaluating the trained neural network at each voxel in the displacement data.

As an example, the displacement data are input to one or more input units in an input layer of the trained neural network, generating output. The output from the input layer is passed to a first hidden layer, generating output. The output of this hidden layers is then passed to the next hidden layer, generating output. This process is repeated for the number of hidden layers in the neural network. The output generated by the last hidden layer includes the one or more mechanical property maps.

In some embodiments, the displacement data can be processed before being input to the trained neural network. For example, the displacement data can have phase unwrapping applied, can have background phase removed, and can be directional filtered.

In some other embodiments, the displacement data are processed to produce different data that are input into the neural network. For example, edge-aware methods can be used to compute the curl on the displacement data, and the curl data can then be smoothed, such as with a quartic kernel without using data from outside the prescribed ROI. Mechanical property maps can then be computed by evaluating a trained neural network in every voxel using the first temporal harmonic of the curl as the inputs to the trained ANN. In these instances, the neural network can be trained on patches of curl data. The three components of the displacements, or of the curl of the displacement, can be inverted separately and then combined into a single mechanical property map (e.g. stiffness map) by computing the weighted average using the squared amplitude of each component.

Figure 5:
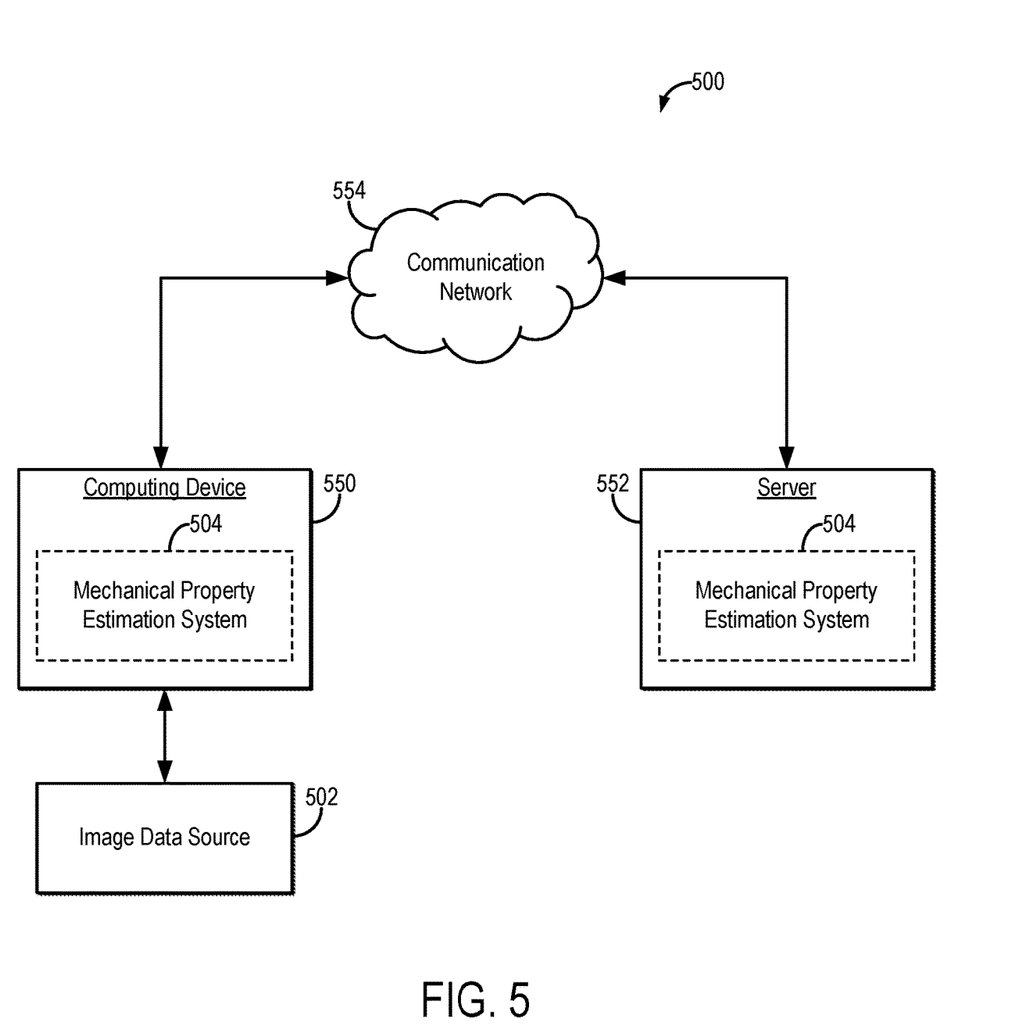
FIG. 5 is a block diagram of an example system that can implement a mechanical property estimation system as described in the present disclosure.

Referring now to FIG. 5, an example of a system 500 for generating mechanical property maps, or otherwise estimating mechanical properties, in accordance with some embodiments of the systems and methods described in the present disclosure is shown. As shown in FIG. 5, a computing device 550 can receive one or more types of data (e.g., displacement data, magnetic resonance image data) from image data source 502, which may be source of magnetic resonance images, displacement data acquired with an MRI system, displacement data acquired with an ultrasound system, displacement data acquired with an optical elastography technique, and so on. In some embodiments, computing device 550 can execute at least a portion of a mechanical property estimation system 504 to generate mechanical property maps, or otherwise or predict mechanical properties, from data received from the image data source 502.

Additionally or alternatively, in some embodiments, the computing device 550 can communicate information about data received from the image data source 502 to a server 552 over a communication network 554, which can execute at least a portion of the mechanical property estimation system 504 to generate mechanical property maps, or otherwise or predict mechanical properties, from data received from the image data source 502. In such embodiments, the server 552 can return information to the computing device 550 (and/or any other suitable computing device) indicative of an output of the mechanical property estimation system 504 to generate mechanical property maps, or otherwise or predict mechanical properties, from data received from the image data source 502. In some aspects, the mechanical property estimation system 504 may implement constructing a neural network (e.g., selecting a type of neural network; selecting a number and type of layers; selecting a number of inputs; selecting weights, biases, transfer functions, or other parameters for one or more layers), training the neural network on training data, and generating mechanical property maps by inputting displacement data or other suitable data to the trained neural network.

In some embodiments, computing device 550 and/or server 552 can be any suitable computing device or combination of devices, such as a desktop computer, a laptop computer, a smartphone, a tablet computer, a wearable computer, a server computer, a virtual machine being executed by a physical computing device, and so on. The computing device 550 and/or server 552 can also reconstruct images from the data.

In some embodiments, image data source 502 can be any suitable source of image data (e.g., measurement data, images reconstructed from measurement data, displacement data), such as an MRI system, an ultrasound system, an optical imaging system, another computing device (e.g., a server storing image data, displacement data, or both), and so on. In some embodiments, image data source 502 can be local to computing device 550. For example, image data source 502 can be incorporated with computing device 550 (e.g., computing device 550 can be configured as part of a device for capturing, scanning, and/or storing images). As another example, image data source 502 can be connected to computing device 550 by a cable, a direct wireless link, and so on. Additionally or alternatively, in some embodiments, image data source 502 can be located locally and/or remotely from computing device 550, and can communicate data to computing device 550 (and/or server 552) via a communication network (e.g., communication network 554).

In some embodiments, communication network 554 can be any suitable communication network or combination of communication networks. For example, communication network 554 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CD MA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 5 can each be any suitable communications link or combination of communications links, such as wired links, fiber optic links, Wi-Fi links, Bluetooth links, cellular links, and so on.

Figure 6:
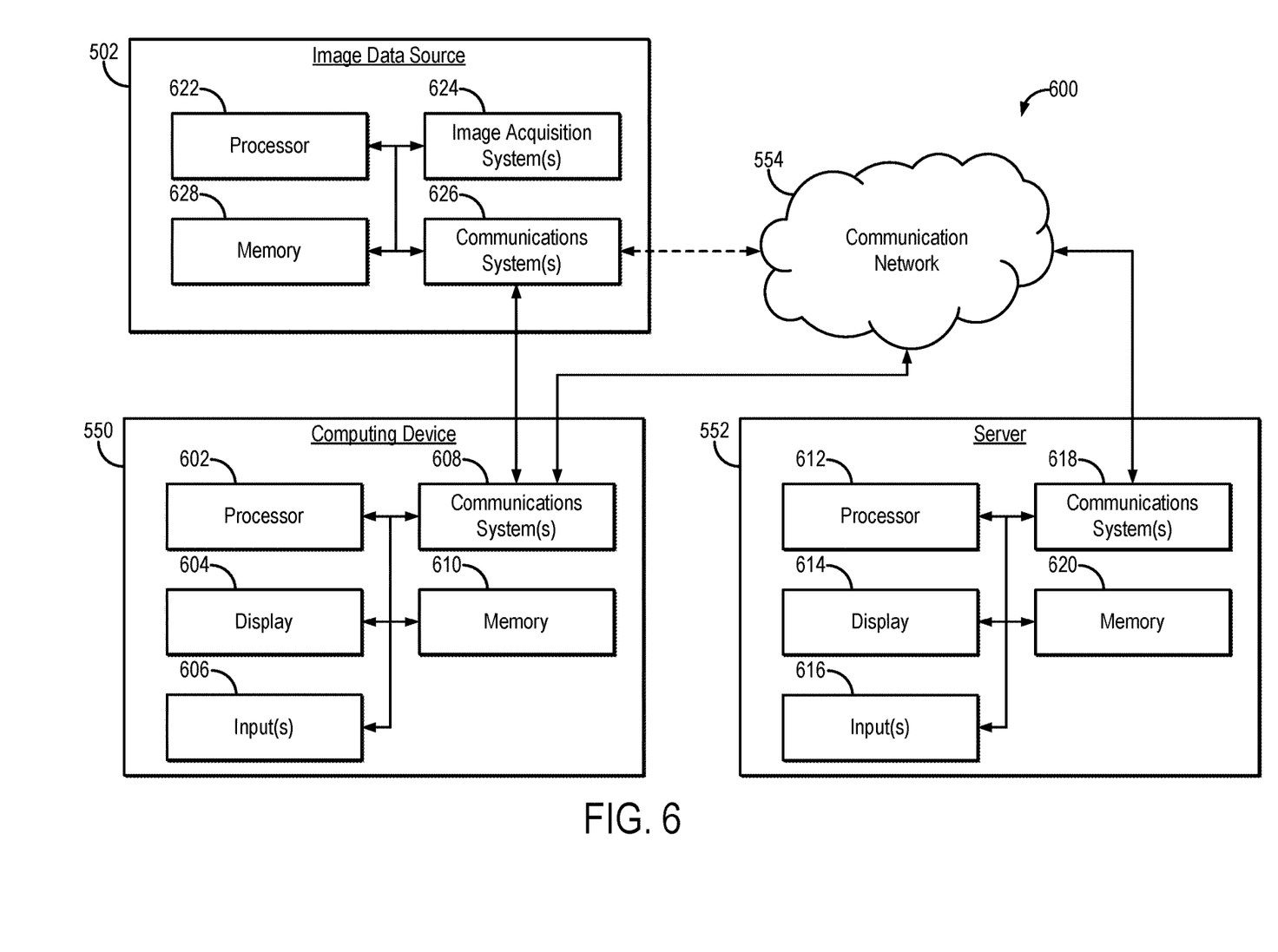
FIG. 6 is a block diagram of example hardware components that can implement the system of FIG. 5.

Referring now to FIG. 6, an example of hardware 600 that can be used to implement image data source 502, computing device 550, and server 554 in accordance with some embodiments of the systems and methods described in the present disclosure is shown. As shown in FIG. 6, in some embodiments, computing device 550 can include a processor 602, a display 604, one or more inputs 606, one or more communication systems 608, and/or memory 610. In some embodiments, processor 602 can be any suitable hardware processor or combination of processors, such as a central processing unit ("CPU"), a graphics processing unit ("GPU"), and so on. In some embodiments, display 604 can include any suitable display devices, such as a computer monitor, a touchscreen, a television, and so on. In some embodiments, inputs 606 can include any suitable input devices and/or sensors that can be used to receive user input, such as a keyboard, a mouse, a touchscreen, a microphone, and so on.

In some embodiments, communications systems 608 can include any suitable hardware, firmware, and/or software for communicating information over communication network 554 and/or any other suitable communication networks. For example, communications systems 608 can include one or more transceivers, one or more communication chips and/or chip sets, and so on. In a more particular example, communications systems 608 can include hardware, firmware and/or software that can be used to establish a Wi-Fi connection, a Bluetooth connection, a cellular connection, an Ethernet connection, and so on.

In some embodiments, memory 610 can include any suitable storage device or devices that can be used to store instructions, values, data, or the like, that can be used, for example, by processor 602 to present content using display 604, to communicate with server 552 via communications system(s) 608, and so on. Memory 610 can include any suitable volatile memory, non-volatile memory, storage, or any suitable combination thereof. For example, memory 610 can include RAM, ROM, EEPROM, one or more flash drives, one or more hard disks, one or more solid state drives, one or more optical drives, and so on. In some embodiments, memory 610 can have encoded thereon, or otherwise stored therein, a computer program for controlling operation of computing device 550. In such embodiments, processor 602 can execute at least a portion of the computer program to present content (e.g., images, user interfaces, graphics, tables), receive content from server 552, transmit information to server 552, and so on.

In some embodiments, server 552 can include a processor 612, a display 614, one or more inputs 616, one or more communications systems 618, and/or memory 620. In some embodiments, processor 612 can be any suitable hardware processor or combination of processors, such as a CPU, a GPU, and so on. In some embodiments, display 614 can include any suitable display devices, such as a computer monitor, a touchscreen, a television, and so on. In some embodiments, inputs 616 can include any suitable input devices and/or sensors that can be used to receive user input, such as a keyboard, a mouse, a touchscreen, a microphone, and so on.

In some embodiments, communications systems 618 can include any suitable hardware, firmware, and/or software for communicating information over communication network 554 and/or any other suitable communication networks. For example, communications systems 618 can include one or more transceivers, one or more communication chips and/or chip sets, and so on. In a more particular example, communications systems 618 can include hardware, firmware and/or software that can be used to establish a Wi-Fi connection, a Bluetooth connection, a cellular connection, an Ethernet connection, and so on.

In some embodiments, memory 620 can include any suitable storage device or devices that can be used to store instructions, values, data, or the like, that can be used, for example, by processor 612 to present content using display 614, to communicate with one or more computing devices 550, and so on. Memory 620 can include any suitable volatile memory, non-volatile memory, storage, or any suitable combination thereof. For example, memory 620 can include RAM, ROM, EEPROM, one or more flash drives, one or more hard disks, one or more solid state drives, one or more optical drives, and so on. In some embodiments, memory 620 can have encoded thereon a server program for controlling operation of server 552. In such embodiments, processor 612 can execute at least a portion of the server program to transmit information and/or content (e.g., data, images, a user interface) to one or more computing devices 550, receive information and/or content from one or more computing devices 550, receive instructions from one or more devices (e.g., a personal computer, a laptop computer, a tablet computer, a smartphone), and so on.

In some embodiments, image data source 502 can include a processor 622, one or more image acquisition systems 624, one or more communications systems 626, and/or memory 628. In some embodiments, processor 622 can be any suitable hardware processor or combination of processors, such as a CPU, a GPU, and so on. In some embodiments, the one or more image acquisition systems 624 are generally configured to acquire data, images, or both, and can include an MRI system, an ultrasound system, or an optical imaging system. Additionally or alternatively, in some embodiments, one or more image acquisition systems 624 can include any suitable hardware, firmware, and/or software for coupling to and/or controlling operations of an MRI system, an ultrasound system, or an optical imaging system. In some embodiments, one or more portions of the one or more image acquisition systems 624 can be removable and/or replaceable.

Note that, although not shown, image data source 502 can include any suitable inputs and/or outputs. For example, image data source 502 can include input devices and/or sensors that can be used to receive user input, such as a keyboard, a mouse, a touchscreen, a microphone, a trackpad, a trackball, and so on. As another example, image data source 502 can include any suitable display devices, such as a computer monitor, a touchscreen, a television, etc., one or more speakers, and so on.

In some embodiments, communications systems 626 can include any suitable hardware, firmware, and/or software for communicating information to computing device 550 (and, in some embodiments, over communication network 554 and/or any other suitable communication networks). For example, communications systems 626 can include one or more transceivers, one or more communication chips and/or chip sets, and so on. In a more particular example, communications systems 626 can include hardware, firmware and/ or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 628 can include any suitable storage device or devices that can be used to store instructions, values, data, or the like, that can be used, for example, by processor 622 to control the one or more image acquisition systems 624, and/or receive data from the one or more image acquisition systems 624; to images from data; present content (e.g., images, a user interface) using a display; communicate with one or more computing devices 550; and so on. Memory 628 can include any suitable volatile memory, non-volatile memory, storage, or any suitable combination thereof. For example, memory 628 can include RAM, ROM, EEPROM, one or more flash drives, one or more hard disks, one or more solid state drives, one or more optical drives, and so on. In some embodiments, memory 628 can have encoded thereon, or otherwise stored therein, a program for controlling operation of image data source 502. In such embodiments, processor 622 can execute at least a portion of the program to generate images, transmit information and/or content (e.g., data, images) to one or more computing devices 550, receive information and/or content from one or more computing devices 550, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Figure 7:
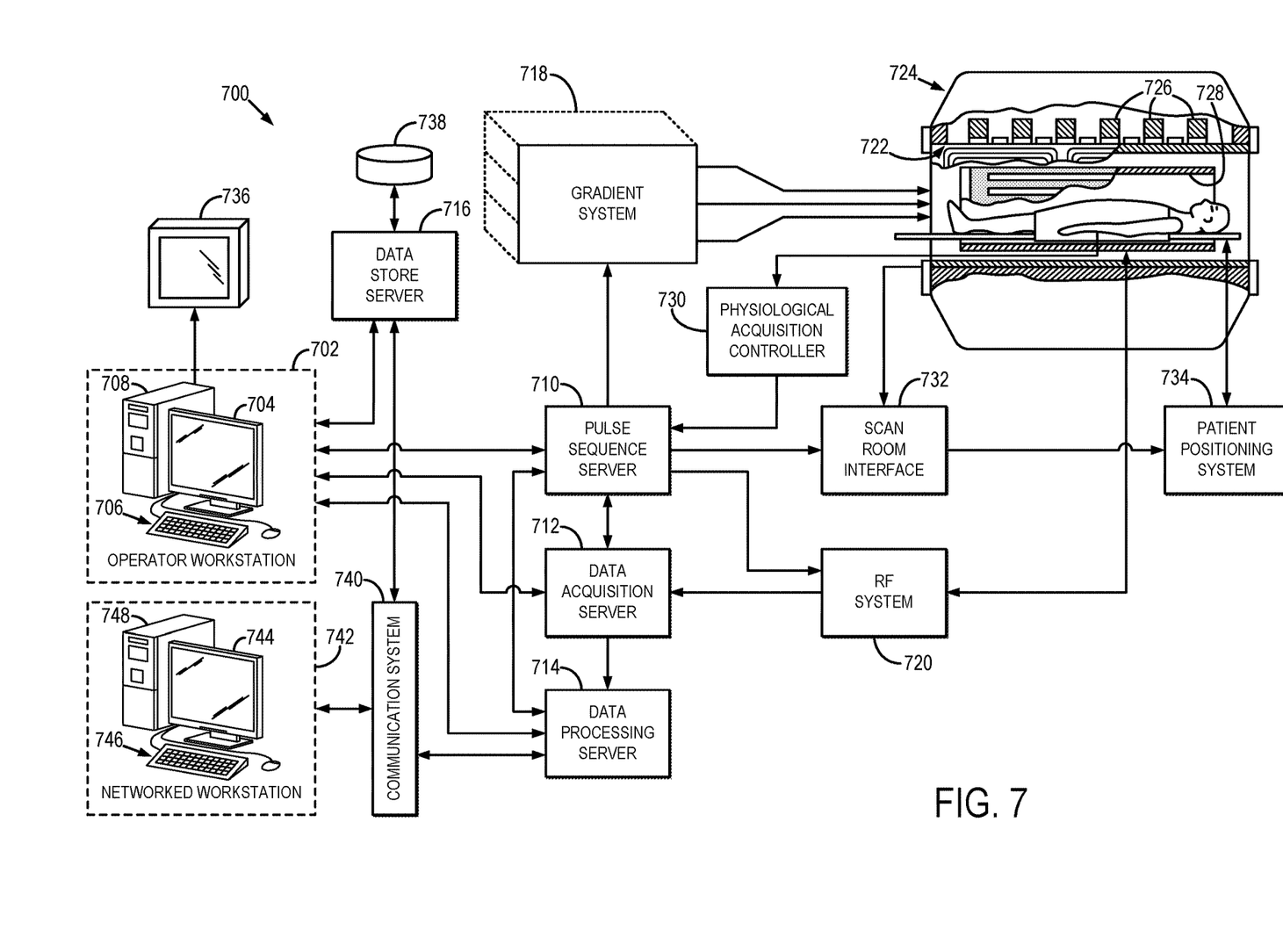
FIG. 7 is a block diagram of an example magnetic resonance imaging ("MRI") system that can implement the methods described in the present disclosure.

Referring particularly now to FIG. 7, an example of an MRI system 700 that can implement the methods described here is illustrated. The MRI system 700 includes an operator workstation 702 that may include a display 704, one or more input devices 706 (e.g., a keyboard, a mouse), and a processor 708. The processor 708 may include a commercially available programmable machine running a commercially available operating system. The operator workstation 702 provides an operator interface that facilitates entering scan parameters into the MRI system 700. The operator workstation 702 may be coupled to different servers, including, for example, a pulse sequence server 710, a data acquisition server 712, a data processing server 714, and a data store server 716. The operator workstation 702 and the servers 710, 712, 714, and 716 may be connected via a communication system 740, which may include wired or wireless network connections.

The pulse sequence server 710 functions in response to instructions provided by the operator workstation 702 to operate a gradient system 718 and a radiofrequency ("RF") system 720. Gradient waveforms for performing a prescribed scan are produced and applied to the gradient system 718, which then excites gradient coils in an assembly 722 to produce the magnetic field gradients $G_x$, $G_y$, and $G_z$ that are used for spatially encoding magnetic resonance signals. The gradient coil assembly 722 forms part of a magnet assembly 724 that includes a polarizing magnet 726 and a whole-body RF coil 728.

RF waveforms are applied by the RF system 720 to the RF coil 728, or a separate local coil to perform the prescribed magnetic resonance pulse sequence. Responsive magnetic resonance signals detected by the RF coil 728, or a separate local coil, are received by the RF system 720. The responsive magnetic resonance signals may be amplified, demodulated, filtered, and digitized under direction of commands produced by the pulse sequence server 710. The RF system 720 includes an RF transmitter for producing a wide variety of RF pulses used in MRI pulse sequences. The RF transmitter is responsive to the prescribed scan and direction from the pulse sequence server 710 to produce RF pulses of the desired frequency, phase, and pulse amplitude waveform. The generated RF pulses may be applied to the whole-body RF coil 728 or to one or more local coils or coil arrays.

The RF system 720 also includes one or more RF receiver channels. An RF receiver channel includes an RF preamplifier that amplifies the magnetic resonance signal received by the coil 728 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \qquad (1);$$

and the phase of the received magnetic resonance signal may also be determined according to the following relationship:

$$\varphi = \tan^{-1}\left(\frac{Q}{I}\right). \qquad (2)$$

The pulse sequence server 710 may receive patient data from a physiological acquisition controller 730. By way of example, the physiological acquisition controller 730 may receive signals from a number of different sensors connected to the patient, including electrocardiograph ("ECG") signals from electrodes, or respiratory signals from a respiratory bellows or other respiratory monitoring devices. These signals may be used by the pulse sequence server 710 to synchronize, or "gate," the performance of the scan with the subject's heart beat or respiration.

The pulse sequence server 710 may also connect to a scan room interface circuit 732 that receives signals from various sensors associated with the condition of the patient and the magnet system. Through the scan room interface circuit 732, a patient positioning system 734 can receive commands to move the patient to desired positions during the scan.

The digitized magnetic resonance signal samples produced by the RF system 720 are received by the data acquisition server 712. The data acquisition server 712 operates in response to instructions downloaded from the operator workstation 702 to receive the real-time magnetic resonance data and provide buffer storage, so that data is not lost by data overrun. In some scans, the data acquisition server 712 passes the acquired magnetic resonance data to the data processor server 714. In scans that require information derived from acquired magnetic resonance data to control the further performance of the scan, the data acquisition server 712 may be programmed to produce such information and convey it to the pulse sequence server 710. For example, during pre-scans, magnetic resonance data may be acquired and used to calibrate the pulse sequence performed by the pulse sequence server 710. As another example, navigator signals may be acquired and used to adjust the operating parameters of the RF system 720 or the gradient system 718, or to control the view order in which k-space is sampled. In still another example, the data acquisition server 712 may also process magnetic resonance signals used to detect the arrival of a contrast agent in a magnetic resonance angiography ("MRA") scan. For example, the data acquisition server 712 may acquire magnetic resonance data and processes it in real-time to produce information that is used to control the scan.

The data processing server 714 receives magnetic resonance data from the data acquisition server 712 and processes the magnetic resonance data in accordance with instructions provided by the operator workstation 702. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 714 are conveyed back to the operator workstation 702 for storage. Real-time images may be stored in a data base memory cache, from which they may be output to operator display 702 or a display 736. Batch mode images or selected real time images may be stored in a host database on disc storage 738. When such images have been reconstructed and transferred to storage, the data processing server 714 may notify the data store server 716 on the operator workstation 702. The operator workstation 702 may be used by an operator to archive the images, produce films, or send the images via a network to other facilities.

The MRI system 700 may also include one or more networked workstations 742. For example, a networked workstation 742 may include a display 744, one or more input devices 746 (e.g., a keyboard, a mouse), and a processor 748. The networked workstation 742 may be located within the same facility as the operator workstation 702, or in a different facility, such as a different healthcare institution or clinic.

The networked workstation 742 may gain remote access to the data processing server 714 or data store server 716 via the communication system 740. Accordingly, multiple networked workstations 742 may have access to the data processing server 714 and the data store server 716. In this manner, magnetic resonance data, reconstructed images, or other data may be exchanged between the data processing server 714 or the data store server 716 and the networked workstations 742, such that the data or images may be remotely processed by a networked workstation 742.

The present disclosure has described one or more preferred embodiments, and it should be appreciated that many equivalents, alternatives, variations, and modifications, aside from those expressly stated, are possible and within the scope of the invention.

The invention claimed is:

1. A method for generating an image that depicts a mechanical property in a tissue of a subject, the steps of the method comprising:
    (a) providing to a computer system, displacement data acquired with a magnetic resonance imaging (MRI) system and depicting displacements caused in a subject by vibratory motion applied to the subject while the data were acquired with the MRI system;
    (b) providing to the computer system, training data representative of displacements caused by vibratory motion propagating in a medium;
    (c) constructing a neural network with the computer system;
    (d) training the neural network on the training data using the computer system;

(e) generating an image that depicts a mechanical property in a tissue of the subject by inputting the displacement data to the trained neural network; and
wherein the training data comprise simulated displacement data.

2. The method as recited in claim 1, wherein the simulated displacement data include data indicative of simulated displacements caused by a single motion source in a volume.

3. The method as recited in claim 1, wherein the simulated displacement data include data indicative of simulated displacements caused by multiple motion sources in a volume.

4. The method as recited in claim 1, wherein the simulated displacement data comprise patches of simulated displacement data, wherein each patch comprises a two-dimensional or three-dimensional array of voxels.

5. The method as recited in claim 1, wherein the training data comprise simulated displacement data that simulates displacements in an inhomogeneous medium.

6. The method as recited in claim 5, wherein the simulated data are generated using a coupled harmonic oscillators simulation.

7. The method as recited in claim 1, wherein the training data comprise at least a portion of the displacement data acquired from the subject.

8. The method as recited in claim 1, wherein the neural network is a feedforward neural network.

9. The method as recited in claim 1, wherein the neural network is a convolutional neural network.

10. The method as recited in claim 1, wherein the displacement data comprises wave images that depict the vibratory motion in the subject.

11. The method as recited in claim 1, wherein the mechanical property is at least one of stiffness, storage modulus, loss modulus, or damping ratio.

12. The method as recited in claim 1, wherein the mechanical property is a poroelastic parameter.

13. The method as recited in claim 1, wherein the neural network comprises a variational sparse coding network.

14. The method as recited in claim 1, wherein the neural network comprises a convolutional sparse coding network.

15. The method as recited in claim 1, wherein the displacement data are representative of transient displacements.

16. The method as recited in claim 1, wherein the displacement data comprise multiple frequency displacement data.

17. The method as recited in claim 1, wherein the displacement data are representative of multiple sources of displacements within the subject.

18. A method for generating an image that depicts a mechanical property in a tissue of a subject, the steps of the method comprising:
(a) providing to a computer system, displacement data acquired with a magnetic resonance imaging (MRI) system and depicting displacements caused in a subject by vibratory motion applied to the subject while the data were acquired with the MRI system;
(b) providing to the computer system, training data representative of displacements caused by vibratory motion propagating in a medium;
(c) constructing a neural network with the computer system;
(d) training the neural network on the training data using the computer system;
(e) generating an image that depicts a mechanical property in a tissue of the subject by inputting the displacement data to the trained neural network; and
wherein the training data include feature data comprising real and imaginary parts of temporal harmonics of displacement data.

19. The method as recited in claim 3, wherein the feature data are scaled to a range of values.

20. A method for generating an image that depicts a mechanical property in a tissue of a subject, the steps of the method comprising:
(a) providing to a computer system, displacement data acquired with a magnetic resonance imaging (MRI) system and depicting displacements caused in a subject by vibratory motion applied to the subject while the data were acquired with the MRI system;
(b) providing to the computer system, training data representative of displacements caused by vibratory motion propagating in a medium;
(c) constructing a neural network with the computer system;
(d) training the neural network on the training data using the computer system;
(e) generating an image that depicts a mechanical property in a tissue of the subject by inputting the displacement data to the trained neural network; and
wherein the neural network is a convolutional neural network.

21. A method for generating an image that depicts a mechanical property in a tissue of a subject, the steps of the method comprising:
(a) providing to a computer system, displacement data acquired with a magnetic resonance imaging (MRI) system and depicting displacements caused in a subject by vibratory motion applied to the subject while the data were acquired with the MRI system;
(b) providing to the computer system, training data representative of displacements caused by vibratory motion propagating in a medium;
(c) constructing a neural network with the computer system;
(d) training the neural network on the training data using the computer system;
(e) generating an image that depicts a mechanical property in a tissue of the subject by inputting the displacement data to the trained neural network; and
wherein the displacement data comprises wave images that depict the vibratory motion in the subject.

22. A method for generating an image that depicts a mechanical property in a tissue of a subject, the steps of the method comprising:
(a) providing to a computer system, displacement data acquired with a magnetic resonance imaging (MRI) system and depicting displacements caused in a subject by vibratory motion applied to the subject while the data were acquired with the MRI system;
(b) providing to the computer system, training data representative of displacements caused by vibratory motion propagating in a medium;
(c) constructing a neural network with the computer system;
(d) training the neural network on the training data using the computer system;
(e) generating an image that depicts a mechanical property in a tissue of the subject by inputting the displacement data to the trained neural network; and
wherein the mechanical property is a poroelastic parameter.

23. A method for generating an image that depicts a mechanical property in a tissue of a subject, the steps of the method comprising:
(a) providing to a computer system, displacement data acquired with a magnetic resonance imaging (MRI) system and depicting displacements caused in a subject by vibratory motion applied to the subject while the data were acquired with the MRI system;
(b) providing to the computer system, training data representative of displacements caused by vibratory motion propagating in a medium;
(c) constructing a neural network with the computer system;
(d) training the neural network on the training data using the computer system;
(e) generating an image that depicts a mechanical property in a tissue of the subject by inputting the displacement data to the trained neural network; and
wherein the neural network comprises at least one of a variational sparse coding network or a convolutional sparse coding network.

24. A method for generating an image that depicts a mechanical property in a tissue of a subject, the steps of the method comprising:
(a) providing to a computer system, displacement data acquired with a magnetic resonance imaging (MRI) system and depicting displacements caused in a subject by vibratory motion applied to the subject while the data were acquired with the MRI system;
(b) providing to the computer system, training data representative of displacements caused by vibratory motion propagating in a medium;
(c) constructing a neural network with the computer system;
(d) training the neural network on the training data using the computer system;
(e) generating an image that depicts a mechanical property in a tissue of the subject by inputting the displacement data to the trained neural network; and
wherein the displacement data are at least one of representative of transient displacements, comprising multiple frequency displacement data, or representative of multiple sources of displacements within the subject.

* * * * *